US00PP27497P2

(12) United States Plant Patent
Hansen

(10) Patent No.: US PP27,497 P2
(45) Date of Patent: Dec. 20, 2016

(54) ***MONARDA* PLANT NAMED 'BUBBLEGUM BLAST'**

(50) Latin Name: *Monarda didyma*
Varietal Denomination: Bubblegum Blast

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 13 days.

(21) Appl. No.: 14/545,863

(22) Filed: Jun. 30, 2015

(51) Int. Cl.
*A01H 5/00* (2006.01)

(52) U.S. Cl.
USPC ..... Plt./455

(58) Field of Classification Search
USPC ..... Plt./455
See application file for complete search history.

*Primary Examiner* — Susan McCormick Ewoldt

(57) ABSTRACT

The new and distinct cultivar of ornamental bee balm plant named *Monarda didyma* 'Bubblegum Blast' has rapid-growing, intermediate height, compact, branching stems, medium to dark green foliage, numerous hot-pink flowers and resistance to powdery mildew.

1 Drawing Sheet

BOTANICAL DESIGNATION AND CULTIVAR DENOMINATION

Botanical classification: *Monarda didyma.*
Variety denomination: 'Bubblegum Blast'.

FEDERAL SPONSORSHIP AND FUNDING

This plant invention was developed without federally sponsored research or development funding.

BACKGROUND OF THE INVENTION

The present invention relates to the new and distinct cultivar of bee balm, botanically known as *Monarda didyma* 'Bubblegum Blast', and hereinafter also referred to solely as the cultivar 'Bubblegum Blast' or the "new plant". The new plant was the subject of an open pollination in summer of 2009 at a wholesale perennial nursery in Zeeland, Mich., USA. Seed was harvested by the inventor on Oct. 6, 2009 and the individual seedling later assigned the breeder identification number H9-43-01. The female or seed parent is *Monarda didyma* 'ACrade' (U.S. Plant Pat. No. 19,580) and the male or pollen parent is unknown but may have been any one of a large number of parents in the general breeding area with the efficiency of insect pollination. The plant was initially subjected to evaluation in the summer of 2011 in trial plots of the same nursery in Zeeland, Mich. The new plant was collected and set apart as a single selected seedling in July of 2012 and passed final evaluation in the summer of 2013.

The plant has been asexually propagated by stem cuttings at the same nursery at the greenhouses in Zeeland, Mich., and the subsequent asexually propagated plants found to be stable and identical to the original selection.

BRIEF SUMMARY OF THE PLANT

*Monarda didyma* 'Bubblegum Blast' is unique from its parents and all other bee balm plants known to the inventor.

The nearest comparison varieties are the parent 'ACrade', 'Pardon My Pink' U.S. Plant Pat. No. 24,244, 'Pink Supreme' U.S. Plant Pat. No. 14,204, 'Petite Delight' U.S. Plant Pat. No. 10,784, 'Pink Lace' U.S. Plant Pat. No. 18,367, 'Marshall's Delight' (not patented) and 'Sugar Lace' U.S. Plant Pat. No. 22,918. 'Bubblegum Blast' is shorter in habit than 'Marshall's Delight' and taller than 'ACrade', 'Pardon My Pink', 'Pink Lace', 'Pink Supreme' and 'Sugar Lace'. 'Petite Delight' has lighter pink flowers while the others are deeper pink or have more purple in flower than 'Bubblegum Blast'.

The following are traits of *Monarda didyma* 'Bubblegum Blast' that in combination distinguish it from all other Bee Balm known to the inventor:

1. Intermediate height, moderate growth rate, winter-hardy, tightly-clumping habit.
2. Medium to dark-green, powdery mildew resistant foliage.
3. Compact hot-pink flowers for a long period in summer.

The table below shows a more concise comparison of the nearest cultivars in the flower color and height traits.

TABLE 1

| MONARDA CULTIVAR | FLOWER COLOR | HEIGHT |
|---|---|---|
| 'ACrade' | purple violet | 40 cm |
| 'Bubblegum Blast' | hot pink | 60 cm |
| 'Marshall's Delight' | medium pink | 92 cm |
| 'Pardon My Pink' | fuchsia pink | 28 cm |
| 'Petite Delight' | light pink-purple | 30 cm |
| 'Pink Lace' | deep pink | 45 cm |
| 'Pink Supreme' | deep pink | 60 cm |
| 'Sugar Lace' | red-purple | 45 cm |

BRIEF DESCRIPTION OF THE DRAWINGS

The photographs of the new plant demonstrate the unique traits of 'Bubblegum Blast' and the overall appearance of the plant at three-years-old in the full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
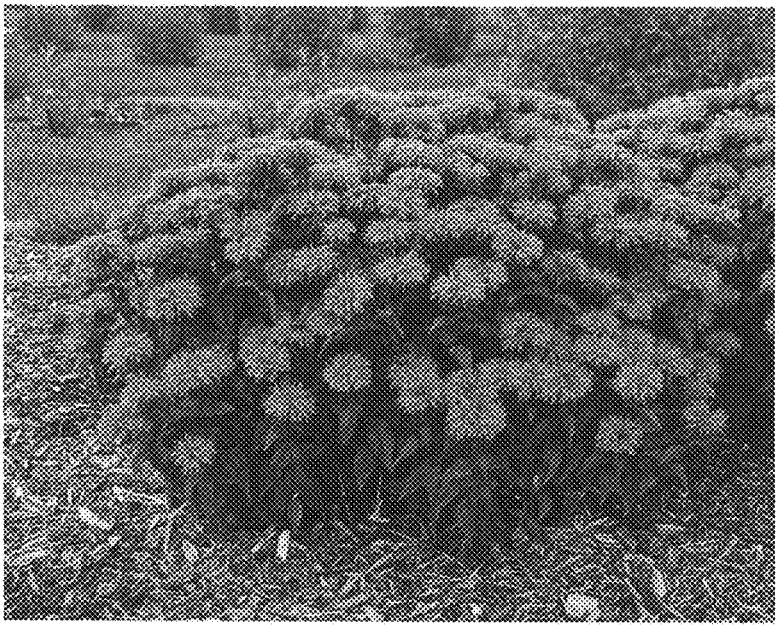
FIG. 1 shows the new plant in flower.
Figure 2:
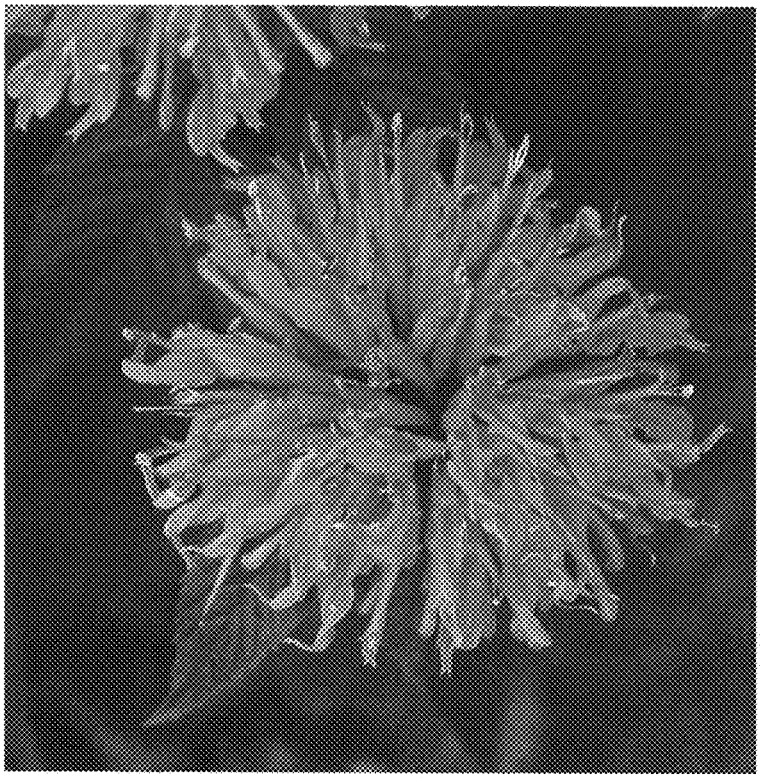
FIG. 2 shows a close-up of the flower.

The following descriptions and color references are based on the 2001 edition of The Royal Horticultural Society Colour Chart except where common dictionary terms are used. *Monarda didyma* 'Bubblegum Blast' has not been observed under all possible environments. The phenotype may vary slightly with different growing environments such as temperature, light, fertility, soil pH, moisture and maturity levels, but without any change in the genotype. The following observations and size descriptions are based on two-year old full-sun grown plants in trial beds at a nursery in Zeeland, Mich. with minimal supplemental fertilizer and water as needed but without plant growth regulators or pinching.

Botanical classification: *Monarda didyma.*

Parentage: Female (seed) parent is Monarda didyma 'ACrade' U.S. Plant Pat. No. 19,580; male (pollen) parent is unknown.

Plant habit: Hardy herbaceous perennial, compact, producing several stems spreading by rhizomes; about 60 cm tall at flowering and about 86 cm wide; flowering begins mid-summer in Michigan and continuing for about 5 to 8 weeks.

Propagation: Stem cuttings.

Time to produce finished crop in 3.8 liter pots: About 7 to 9 weeks; moderately fast rate of growth.

Root: Fine, fibrous and freely branching; color creamy white to tan depending on soil type.

Leaves: Simple, lanceolate, opposite, serrated, puberulent above and below; surface lustrous above, semi-lustrous to matte below; acute apex, ovate to rounded base; average about 7.0 cm long and about 3.3 cm wide.

Leaf color: Young adaxial surface nearest RHS 137C and abaxial between RHS 146B and RHS 138B; older leaves between RHS 139A and RHS 136A adaxial and abaxial surface of older leaves nearest RHS 138C.

Foliage fragrance: Pleasantly lemony.

Veins: Pinnate; pubescent below with minute puberulent above, slightly sunken above and raised below.

Vein color: Adaxial midrib nearest RHS 136A, center portion of lateral veins nearest RHS 135A above with distal vein portion nearest RHS 136A; abaxial midrib and center portion of lateral veins between RHS 157C and RHS 145C with distal lateral veins blending to leaf base color of RHS 138C on perimeter.

Petiole: Pubescent, slightly concaved above, about 10.0 mm long and 2.0 mm across.

Petiole color: Nearest RHS 144C above and nearest RHS 144D underneath.

Stems: Squared, puberulent, densely pubescent at nodes; 4.0 to 7.0 mm across at base, average about 5.0 mm across; about 50 stems per plant.

Stem color: Nearest RHS 145B in upper portion with basal portion and directly under flower head developing tinting of between RHS N187C and RHS N187B.

Nodes: 10 to 12 per stem; densely pubescent; average internode length about 5.0 cm, closer at base; node color same as surrounding stem.

Flowers: Single labiate flowers arranged in terminal globular head about 7.0 cm across and 4.0 cm tall opening from the center and progressing outwardly and down; persisting about 5 days in Michigan; numerous, about 300 flowers per head; self-cleaning.

Flower fragrance: Moderately spicy.

Buds one to two days prior to opening: Narrowly oblanceolate, curved downward; about 2.2 cm long and 3.0 mm diameter.

Bud color one to two days prior to opening: Nearest RHS N66A in distal one third with a lighter base of white, lighter than RHS N155D or RHS 155D.

Petals: Labiate, curved downward; split in two in the distal 1.3 cm with upper lip fused into a hood about 3.3 cm long and 2.5 mm diameter; lower lip about 3.5 cm long comprising three lobes including two side lobes about 1.0 mm long with rounded apex and center lobe about 4.0 to 5.0 mm long split in the distal 1.0 mm with acute apex, curled up and back underneath almost to 270 degrees; both lobes glandular and pubescent outer surfaces with fine hairs the same color as petals; both lobes glabrous on inner surfaces.

Petal color: Color of all petals on both surfaces nearest RHS 61B with basal 6.0 mm white, lighter than RHS 155D or RHS N155D.

Filaments: Two, about 3.2 cm long by 0.7 mm diameter.

Filament color: Lighter than RHS 155D except gradually developing tinting in the distal 4.0 mm to lighter than RHS 61D just before anther.

Anther: Oblong elliptic, dorsifixed, longitudinal; about 2.7 mm long and about 1.0 mm across.

Anther color: Between RHS 45C and RHS 53C along the longitudinal dehiscence line and nearest RHS 39D along center and point of attachment of filament.

Pollen: Abundant, elliptic to globose, less than 0.1 mm; color nearest RHS 15D.

Pistil: One per flower.

Style: About 3.8 cm by about 0.25 mm; base color nearest RHS N155D developing tinting increasing at distal end to nearest RHS 61B.

Stigma: Split in two in the distal 2.0 mm, less than 0.25 mm in diameter; RHS 64A.

Ovary: 1.0 mm by 0.75 mm, between RHS 143D and RHS 144B.

Sepals: Five, entire, apiculate apex, base fused forming corolla about 9.0 mm long split in about the apical 2.0 mm, about 2.0 mm diameter at base and about 3.0 mm diameter at distal end; apex glandular and with minute hairs on outer surface.

Sepal color: Apical margin nearest RHS 146D with tinting of between RHS 185A and RHS N186C distally, along fusion lines and in areas of more intense light exposure.

Peduncle: Pubescent, stiff, strong, erect, squared to about 6.0 mm across and about 55.0 cm long.

Peduncle color: Nearest RHS 138A; about 50 per plant; naturally branched at nodes.

Bracts: Five to eight subtending flower head; acute to narrowly acute apex with sessile and truncate base; to about 1.5 cm and about 1.2 cm wide at base, size decreasing distally.

Bract color: Lowest bracts same color as leaves; distally abaxial and adaxial becoming more tinted at apex and margins with RHS N186C; veins both surfaces same color as surrounding bract.

Fruit: Single nutlet, elliptical, about 1.0 mm long and 0.7 mm wide.

Hardiness: The new plant grows best with plenty of moisture and adequate drainage; hardy to at least from USDA zone 4 through 8.

Disease and pest resistance: Demonstrated powdery mildew resistance in side by side comparison at least equal that of those cultivars listed in Table 1.

I claim:

1. A new and distinct plant cultivar *Monarda didyma* 'Bubblegum Blast', as herein described and illustrated, resistant to powdery mildew and suitable for the garden landscape, or as a potted plant, patio, and for cut flower arrangements.

* * * * *